US007633631B2

(12) United States Patent
Fukutake

(10) Patent No.: US 7,633,631 B2
(45) Date of Patent: Dec. 15, 2009

(54) THREE-DIMENSIONAL MICROSCOPE AND METHOD FOR OBTAINING THREE-DIMENSIONAL IMAGE

(75) Inventor: Naoki Fukutake, Tokyo (JP)

(73) Assignee: Nikon Corporation, Tokyo (JP)

( * ) Notice: Subject to any disclaimer, the term of this patent is extended or adjusted under 35 U.S.C. 154(b) by 87 days.

(21) Appl. No.: 12/050,645

(22) Filed: Mar. 18, 2008

(65) Prior Publication Data

US 2008/0259345 A1 Oct. 23, 2008

Related U.S. Application Data

(60) Provisional application No. 60/907,489, filed on Apr. 4, 2007, provisional application No. 60/960,377, filed on Sep. 27, 2007.

(51) Int. Cl.
*G01B 9/02* (2006.01)
*G01B 11/02* (2006.01)
*G01D 5/36* (2006.01)

(52) U.S. Cl. .................. 356/521; 356/511; 250/237 G

(58) Field of Classification Search ............ 356/521, 356/489, 495, 511, 512, 515; 250/237 G
See application file for complete search history.

(56) References Cited

U.S. PATENT DOCUMENTS

| | | | | |
|---|---|---|---|---|
| 5,532,814 A | * | 7/1996 | Cha | ............... 356/28.5 |
| 5,668,648 A | * | 9/1997 | Saito et al. | ............... 359/9 |
| 6,618,190 B2 | * | 9/2003 | Kitamura et al. | ............ 359/316 |
| 6,621,605 B1 | * | 9/2003 | Grossetie et al. | ............... 359/9 |
| 7,161,721 B2 | * | 1/2007 | Young | ............... 359/9 |
| 7,486,406 B2 | * | 2/2009 | Kim | ............ 356/497 |
| 2002/0027702 A1 | * | 3/2002 | Kitamura et al. | ............ 359/276 |
| 2007/0216906 A1 | * | 9/2007 | Javidi et al. | ............... 356/457 |
| 2008/0259345 A1 | * | 10/2008 | Fukutake | ............ 356/450 |

OTHER PUBLICATIONS

Cuche, et al. "Simultaneous amplitude-contrast and quantitative phase-contrast microscopy by numerical reconstruction of Fresnel off-axis holograms", Applied Optics, vol. 38, No. 34, Dec. 1, 1999, pp. 6994-7001.

* cited by examiner

*Primary Examiner*—Patrick J Connolly
(74) *Attorney, Agent, or Firm*—Morgan, Lewis & Bockius LLP

(57) ABSTRACT

A microscope which has a high three-dimensional resolution, does not require specimens to be stained and is easy to operate, is presented. The three-dimensional microscope includes a first optical system for illuminating an object with lights in a plurality of illuminating directions, one direction after another; an imaging section; a second optical system for guiding diffracted lights generated by the object and reference lights to the imaging section that obtains interference images of the diffracted lights and the reference lights; and a processor for generating a three-dimensional image using the interference images for respective illuminating directions, obtained by the imaging section. The processor obtains complex amplitudes of the diffracted lights from the interference images for respective illuminating directions and generates the three-dimensional image of the object from the complex amplitudes.

16 Claims, 10 Drawing Sheets

THREE-DIMENSIONAL MICROSCOPE AND METHOD FOR OBTAINING THREE-DIMENSIONAL IMAGE

This application claims the benefit of U.S. Provisional Application No. 60/907,489, filed Apr. 4, 2007, and U.S. Provisional Application No. 60/960,377, filed Sep. 27, 2007.

TECHNICAL FIELD

The present invention relates to a three-dimensional microscope and a method for obtaining a three-dimensional image.

BACKGROUND ART

Confocal microscopes are widely used in biology, medical science, pharmaceutical science and the like. Confocal microscopes usually require specimens to be stained, and therefore are not appropriate for observation of living tissues. With confocal microscopes, images can be obtained also from unstained specimens. However, in the case of weakly scattering objects such as biological specimens, confocal transmission microscopes cannot reproduce high contrast images, while confocal reflection microscopes cannot reproduce precise images of the objects.

Nonlinear optical microscopes have been developed as tools that do not require staining specimens before observation. In nonlinear optical microscopes, the second harmonic generation (SHG) signal, the third harmonic generation (THG) signal, the coherent anti-Stokes Raman scattering (CARS) signal or the like is used. Nonlinear optical microscopes, however, are not easy to operate, because they employ a high power pulse laser as a light source.

Phase contrast microscopes, which can convert a phase object into a high contrast irradiance image, are most powerful tools to observe biological specimens. However, they can provide two-dimensional images alone.

Holography can provide three-dimensional images, but resolution is not sufficiently high Microscopy using holography is described in a non-patent document, Etienne Cuche, Pierre Marquet and Christian Depeursinge, "Simultaneous amplitude-contrast and quantitative phase-contrast microscopy by numerical reconstruction of Fresnel off-axis holograms", Appl. Opt. 38, 6994-7001 (1999), for example.

Optical coherence tomography (OCT) is an exquisite device for biological specimens. However, in OCT, resolution in the depth direction depends on a spectrum width of a light source, and therefore the development of a broadband light source is indispensable in order to gain high resolution in the depth direction.

On the other hand, in industrial applications, there is a need for generating an image of defects inside glass, for example. However, a device which can separately generate a three-dimensional image of refractive index distribution and that of absorptance distribution, has not been developed.

In biology, medical science, pharmaceutical science and the like, there is a need for a microscope which has a high three-dimensional resolution, does not require specimens to be stained and is easy to operate.

Further, in industrial applications, there is a need for a microscope separately generating a three-dimensional image of refractive index distribution and that of absorptance distribution.

DISCLOSURE OF INVENTION

According to a first aspect illustrating the present invention, a three-dimensional microscope as follows is presented. The three-dimensional microscope includes a first optical system for illuminating an object with lights in a plurality of illuminating directions, one direction after another; an imaging section; a second optical system for guiding diffracted lights generated by the object and reference lights to the imaging section that obtains interference images of the diffracted lights and the reference lights; and a processor for generating a three-dimensional image using the interference images for respective illuminating directions, obtained by the imaging section. The processor obtains complex amplitudes of the diffracted lights from the interference images for respective illuminating directions and generates the three-dimensional image of the object from the complex amplitudes.

According to a second aspect illustrating the present invention, a method for generating a three-dimensional image of an object using digital holography is presented. The method includes illuminating the object in a plurality of illuminating directions, one direction after another; obtaining interference images of diffracted lights generated by the object and reference lights, for respective illuminating directions; obtaining complex amplitudes of the diffracted lights from the interference images obtained for respective illuminating directions; and generating the three-dimensional image of the object from the complex amplitudes.

According to the present invention, a microscope which has a high three-dimensional resolution, does not require specimens to be stained and is easy to operate, can be obtained.

BEST MODE FOR CARRYING OUT THE INVENTION

Figure 1:
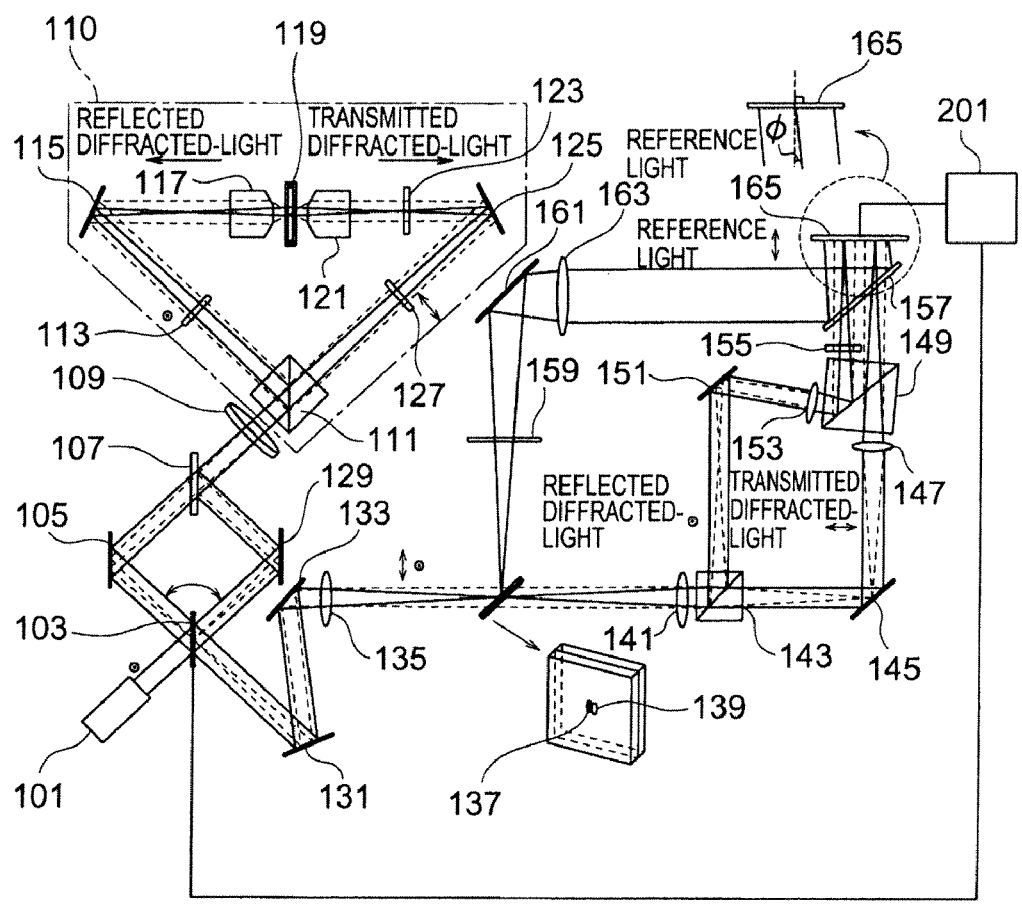
FIG. 1 shows a schematic of a 3-D (three-dimensional) microscopy instrument according to an embodiment of the claimed invention.

FIG. 1 shows a schematic of a 3-D (three-dimensional) microscopy instrument according to an embodiment of the claimed invention.

In the 3-D microscope according to the embodiment, light from a light source 101 is converted into plane wave and a specimen object (hereinafter referred to merely as object) is illuminated by the plane wave to generate hologram data (interference images) through interference between object light and reference light on a two-dimensional imaging device 165 in a Fourier plane of the object. When the object is illuminated by the light from the light source 101, illuminating direction is changed by a scanning mirror (double-sided mirror) 103 which is tiltable to generate and obtain hologram data in each illuminating direction. The hologram data in each illuminating direction obtained by the two-dimensional imaging device 165, is processed by a processor 201 to reconstruct a 3-D image of the object. Further detailed description is below.

Any two successive lenses in the optical system shown in FIG. 1 compose infinite image-formation systems.

A stable near-infrared laser (having a wave length of 850 nm) with a sufficiently long coherence length is used as the light source 101.

The light generated by the light source 101 and used by a first optical system for illuminating the object will be described below. The direction of the polarization of the light from the light source 101 is perpendicular to the plane of the drawing (S-polarization). The light from the light source 101 is reflected on the scanning mirror 103 and a mirror 105 and further reflected on a polarized beam splitter 111 after having passed through a beam splitter 107 and a second objective lens 109. Then the light from the light source 101 is reflected on a mirror 115 after having passed through a polarizing element 113 and is used to illuminate the object in a specimen holder 119 as a plane wave after having passed through one 117 of the two first objective lenses. The polarizing element 113 is provided to remove noise.

The scanning mirror 103 is made tiltable in such a way that two-dimensional scanning with the light from the light source 101 on the object in the specimen holder 119 can be carried out. The maximum angle of incidence for the object of the light from the light source 101 is approximately 64 degrees and a numerical aperture (NA) of the first objective lens on the object side is 1.2 in water. Since the focal length of the second objective lens 109 is 60 times as long as that of the primary objective lens 117, the maximum tilting angle of the scanning mirror 103 is approximately 1 degree.

0-order light which passes thorough the object without being scattered by the object will be described below. The 0-order light passes thorough the other 121 of the two first objective lenses and a half-wave plate 123. Polarization of the 0-order light is changed to p-polarization by passing thorough the half-wave plate 123. Then, the 0-order light is reflected on a mirror 125, passes through a polarizing element 127, the polarizing beam splitter 111 and the second objective lens 109 and arrives on the scanning mirror 103 after having been reflected on the beam splitter 107 and a mirror 129. The polarizing element 127 is provided to remove noise. The center of the scanning mirror 103 is placed at a conjugate point of the center of the specimen object. The direction of the 0-order light having been reflected on the scanning mirror (double-sided mirror) 113 is set to the same direction as that of light reflected on the scanning mirror 113 which is not tilted. That is, the direction of the 0-order light is kept unchanged independently of a tilting angle of the scanning mirror 103. Then, the 0-order light arrives on a micromirror 137 having a small transmittance with a diameter of approximately 200 µm. The micromirror 137 is located in a Fourier plane of the confocal plane of the two first objective lenses (117 and 121). The confocal plane is the center plane of the object. The majority of the 0-order light is reflected by the micromirror 137 and is used as a reference light after having been collimated by a collimator lens 163. Thus, the 0-order light arrives on the two-dimensional imaging device 165 by a second optical system. A portion of the 0-order light that has passed through the micromirror 137 will be described later.

Transmitted diffracted-light which has been scattered by the object will be described below. The transmitted diffracted-light travels along a path similar to that of the 0-order light. A portion (low-frequency component) of the transmitted diffracted-light is removed by the micromirror 137 located in a Fourier plane of the confocal plane of the two first objective lenses (117 and 121). The other portion of the transmitted diffracted-light travels without being reflected by the micromirror 137, passes through polarizing beam splitters 143 and 149 and arrives on the two-dimensional imaging device 165 located in a Fourier plane of the confocal plane of the two first objective lenses (117 and 121) or at a conjugate position of the micromirror 137. Thus, the transmitted diffracted-light arrives on the two-dimensional imaging device 165 by the second optical system.

A portion of the 0-order light having passed thorough the micromirror 137 having a small transmittance passes through a quarter-wave plate 139. The portion of the 0-order light is circularly polarized after having passed the quarter-wave plate 139 and is split into two components by the polarizing beam splitter 143. One of the two components arrives on the two-dimensional imaging device 165 together with the transmitted diffracted-light, while the other arrives there together with the reflected diffracted-light.

Figure 2:
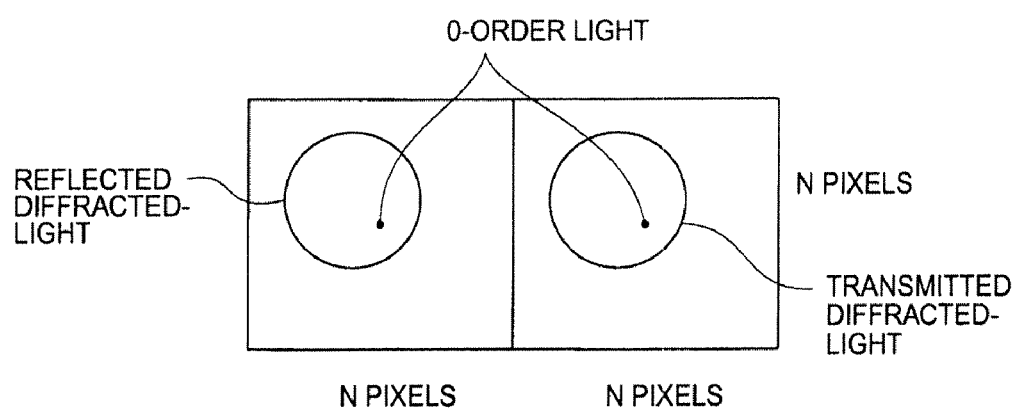
FIG. 2 shows a schematic of the two-dimensional imaging device.

FIG. 2 shows a schematic of the two-dimensional imaging device 165. The two-dimensional imaging device 165 contains an imaging device for transmitted diffracted-light and that for reflected diffracted-light. The two-dimensional imaging device 165 may be a digital camera including CCD or CMOS, for example. The imaging device for transmitted diffracted-light and that for reflected diffracted-light respectively may have 1024×1024 pixels, for example. The transmitted diffracted-light, reflected diffracted-light and the reference light are p-polarized on the observation plane of the two-dimensional imaging device 165. Accordingly, interference between the transmitted diffracted-light and the reference light and interference between the reflected diffracted-light and the reference light will occur so that hologram data can be obtained by the imaging device for transmitted diffracted-light and that for reflected diffracted-light.

The center of the scanning mirror is located at a conjugate point of the center of the specimen object on the optical axis. Accordingly, the transmitted diffracted-light and the reflected diffracted-light are kept to be normally incident on the two-dimensional imaging device 165 even when illuminating direction of a light from the light source 101 to the specimen object is changed by the scanning mirror. When illuminating direction of a light from the light source 101 to the specimen object is changed, a circular range of the transmitted diffracted-light on the imaging device for transmitted diffracted-light moves on the device and a circular range of the reflected diffracted-light on the imaging device for reflected diffracted-light moves on the device. As shown in FIG. 2, the 0-order light reference light) is fixed at the center of the observation plane of the imaging device for transmitted diffracted-light and at that of the imaging device for reflected diffracted-light. The direction of the 0-order light (reference light) is kept constant independently of a tilting angle of the scanning mirror 103 and is always reflected at the center of the micromirror 137. Angle of incidence on the two-dimensional imaging device 165 of the 0-order light (reference light) remains unchanged even when illuminating direction of a light from the light source 101 to the specimen object is changed. Hologram data are obtained for each illuminating direction by the imaging device for transmitted diffracted-light and that for reflected diffracted-light while changing illuminating direction of a light from the light source 101 to the specimen.

Figure 3:
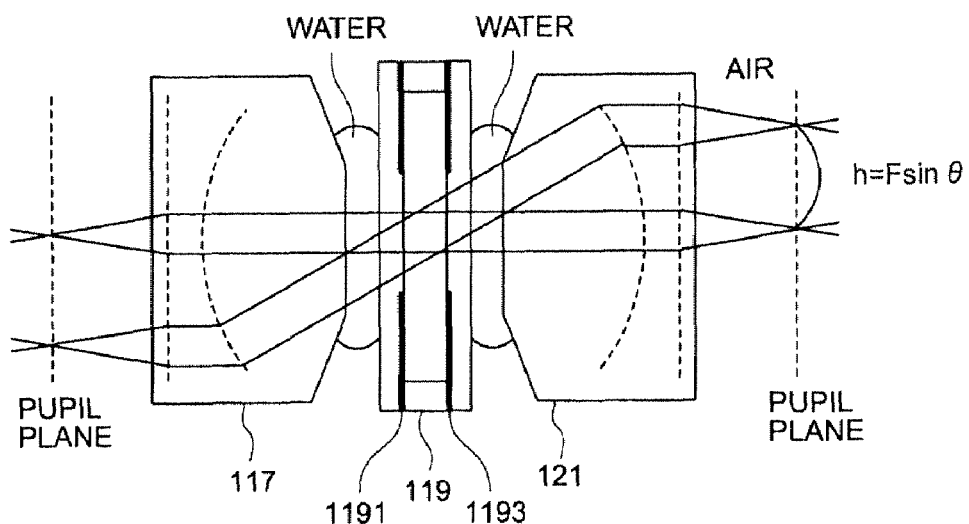
FIG. 3 shows a sample holder and two primary objective lenses.

FIG. 3 shows a sample holder 119 and two primary objective lenses (117 and 121). The primary objective lenses in this embodiment are Fourier lenses, in which the aberration of pupil is corrected properly and the condition $$h = F \sin \theta$$

is satisfied, where h represents the height of the principal ray on the pupil plane, F denotes the focal length, and θ stands for the angle of the principal ray emitted from the central point on the object plane to the optical axis (see FIG. 3). Numerical aperture (NA) on the object side of the primary objective lenses (117 and 121) is 1.2 in water, while NA on the detector side is 0.0075. The focal length of the second objective lens 109 is 200 mm. If the magnification of the primary objective lenses is 60×, the focal length of the primary objective lenses (117 and 121) is about 4.4 mm in water. The field of view in the specimen is approximately 50 μm. The two-dimensional imaging device 165 is set to be conjugate to the pupil planes of the primary objective lenses (117 and 121). If it is assumed that the optical system between the pupil planes of the primary objective lenses (117 and 121) and the detector plane comprises the image-formation system of magnification β, the following relation can be obtained.

$$NA_0 \cdot F = \mu N / 4\beta$$

where $NA_0$ represents numerical aperture (NA) on the object side of the primary objective lenses (117 and 121), μ represents the size of a pixel of the digital camera and N denotes the number of the pixels along a side of the two-dimensional imaging device 165. The length of the side of the two-dimensional imaging device 165 is μN, which is twice as long as the diameter of a circular area of the scattered wave on the two-dimensional imaging device 165.

The observable volume of the specimen is limited by two circular apertures of the aperture stops (1191 and 1193) on both sides of the sample. The diameters of the apertures are three times as large as that of the cross section of the illuminating beam, which is three times as large as the thickness of the specimen. The illuminating beam is converted into a plane wave and is incident on the specimen after converging onto a point in the pupil plane of the primary objective lens 117. The cross section of the illuminating beam on the aperture plane is a circle that is independent of the incident angle, which is one of the features of the Fourier lens (see FIG. 3). The NA of the scattered wave in the pupil plane of the primary objective lens 121 is confined by the apertures to be three times as large as the NA of the 0-order light.

Intensity pattern of light (hologram data) generated by interference of the diffracted light and the reference light is detected on the detection plane of the two-dimensional imaging device 165, and the intensity pattern is converted into amplitude of the diffracted light by digital holography. When the incident angle of the reference wave to the normal of the detection plane is represented as φ shown in FIG. 1, the angle is so adjusted that the following equation is satisfied.

$$\lambda / \sin \phi = 4\mu$$

where λ is a wave length of the reference light and μ is a width of a pixel of the two-dimensional imaging device 165. In other words, the adjustment is made in such a way that a unit cycle of the phase of the reference wave on the detection plane corresponds to four pixels. The difference in spatial frequency corresponding to a side of the imaging device for transmitted diffracted light and that for reflected diffracted light shown in FIG. 2 is set to $$4NA_0/\lambda.$$

$NA_0$ represents numerical aperture (NA) on the object side of the primary objective lenses (117 and 121). The size of the object D in real space, which corresponds to Fourier transform of the spatial frequency mentioned above, is $$D = \lambda N / 4 NA_0 = F \lambda \beta / \mu$$

N represents the number of pixels along a side of the imaging device for transmitted diffracted light and that for reflected diffracted light. The relationship between the diameter of the circular apertures R of the aperture stops (1191 and 1193) and the size of the object D is represented as follows.

$$R = 3D/4$$

Assuming that
$\lambda = 850$ (nm)
$N = 1024$
$NA_0 = 1.2$ the size of the reconstructed object in real space 4/D is approximately 45 μm. The resolution $\lambda/(2NA_0)$ is 354 nm.

In the embodiment hologram data are obtained by two-dimensional scanning of illuminating light on the specimen object and a three-dimensional image of the specimen is generated based on the hologram data. If the size of the 3-D matrix for the image is $256^3$, $128^2 \times \pi/4$ scanning directions (illuminating directions) are required for maximum resolution, where the coefficient $\pi/4$ implies the circular pupil. The number of scanning directions can be reduced by balancing the quality of the image with the scanning time.

A method in which a three-dimensional image is generated based on the hologram data will be described below.

Light scattering amplitude (complex amplitude) of a three-dimensional object $$O(x,y,z)$$

is given by the following equation.

$$O(x,y,z) = 1 + \epsilon(i\alpha(x,y,z) - \beta(x,y,z))(\epsilon \ll 1) \quad (1)$$

The coefficient ε stands for a sufficiently small real number. The term $$\alpha(x,y,z) \propto n(x,y,z) - 1$$

stands for light scattering amplitude caused by absorptance distribution, while the term $$n(x,y,z)$$

stands for distribution of relative refractive index with respect to an average refractive index. The term $$\beta(x,y,z)$$

stands for absorptance distribution. Phase-shift between scattered light generated by absorptance distribution and that generated by refractive index distribution is π/2. 0-order light which has passed through the object without being scattered by the object, corresponds to the first term "1" on the right-hand side of Equation (1).

Hologram data obtained by observing amplitude of the scattered light on the Fourier plane (detection plane of the two-dimensional imaging device 165), correspond to Fourier transform of $$O(x,y,z)$$

A portion of the hologram data corresponding to the 0-order light is a delta function at the original point of the coordinate system.

A visualized 3-D image corresponds to a square of the modulus of the scattering amplitude O(x,y,z).

The square of the modulus of the scattering amplitude is represented by the following equation.

$$|O(x, y, z)|^2 = 1 + \varepsilon(i\alpha(x, y, z) - \beta(x, y, z)) + \qquad (2)$$
$$\varepsilon(-i\alpha(x, y, z) - \beta(x, y, z))$$
$$= 1 - 2\varepsilon\beta(x, y, z)$$

The equation contains DC (direct current) component with absorptance distribution. A higher-contrast image can be obtained by suppressing the DC component. The terms of a square of $\epsilon$ are sufficiently small and therefore have been ignored.

On the other hand, the square of that obtained by shifting phase of the scattering amplitude by $\pi/2$ is represented by the following equation.

$$|O(x, y, z)|^2 = |-i + \varepsilon(i\alpha(x, y, z) - \beta(x, y, z))|^2 \qquad (3)$$
$$= 1 + i\varepsilon(i\alpha(x, y, z) - \beta(x, y, z)) -$$
$$i\varepsilon(-i\alpha(x, y, z) - \beta(x, y, z))$$
$$= 1 - 2\varepsilon\alpha(x, y, z)$$

The equation contains DC (direct current) component with distribution of refractive index. A higher-contrast image can be obtained by suppressing the DC component. The terms of a square of $\epsilon$ are sufficiently small and therefore have been ignored.

Thus, a 3-D image of absorptance distribution and that of refractive index distribution can be separately generated according to Equations (2) and (3).

Figure 4:
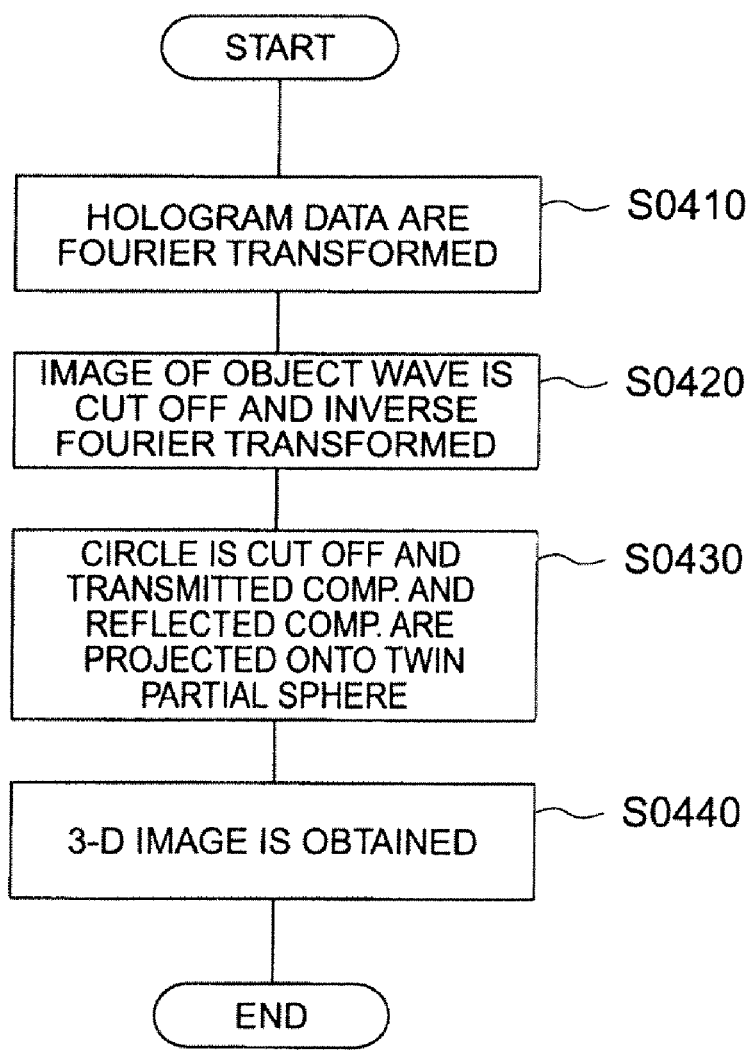
FIG. 4 is a flowchart showing a method by which a 3-D image is generated from hologram data.
Figure 5:
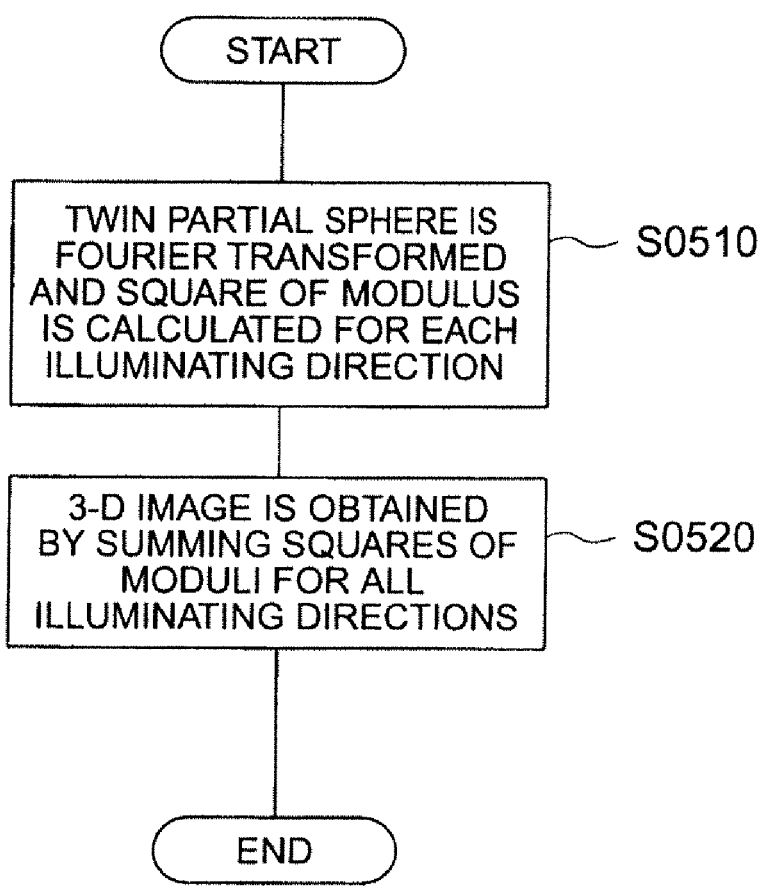
FIG. 5 is a flowchart showing a method by which a 3-D image is generated from hologram data.
Figure 6:
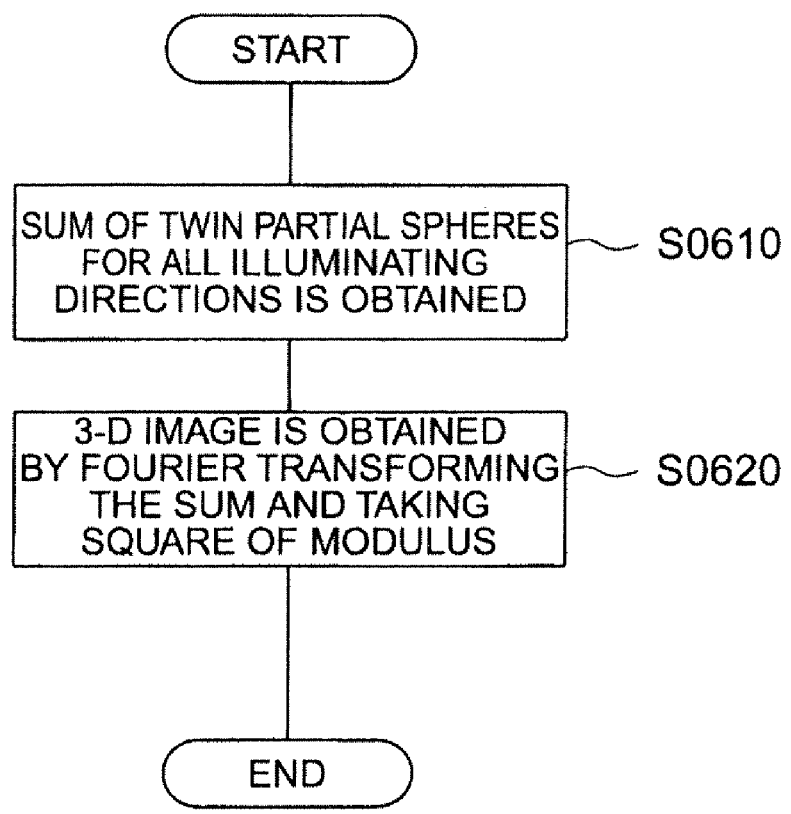
FIG. 6 is a flowchart showing a method by which a 3-D image is generated from hologram data.

FIGS. 4 to 6 are flowcharts showing a method by which a 3-D image is generated from hologram data. The method shown in FIGS. 4 to 6 is carried out by a processor 201. The processor 201 adjusts the scanning mirror to determine an illuminating direction and receives hologram data of each illuminating direction from the two-dimensional imaging device 165.

FIGS. 7 and 8 illustrate a method by which a 3-D image is generated firm hologram data.

In step S0410 of FIG. 4, the hologram data are Fourier transformed. After hologram data for transmitted scattered-lights and reflected scattered-lights generated by the lights in all the illuminating directions are acquired through the two-dimensional imaging device 165, the hologram data of N×N pixels are Fourier transformed in the processor 201.

Figure 7A:
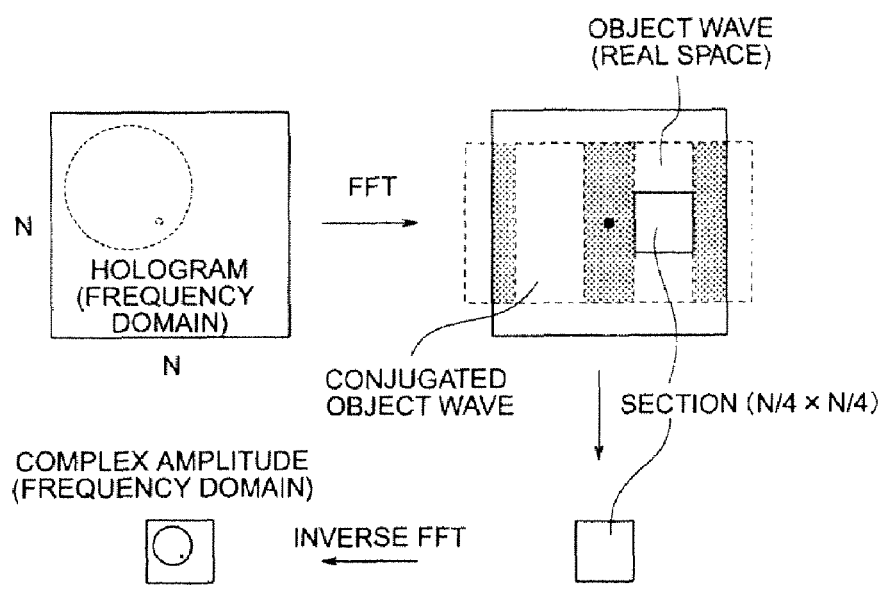
FIG. 7A illustrates a method by which a 3-D image is generated from hologram data.

As a result of that computation, the complex amplitude of the object wave is obtained on one side at the matrix and a conjugated wave appears on another side, as shown in the upper right side of FIG. 7A. FIG. 7A shows component of transmitted diffracted-light alone, omitting component of reflected diffracted-light. While the object wave and the conjugated wave overlap, due to the relation of $R=3D/4$, the central areas of the object and conjugated waves of the size of N/4 do not overlap. Because the irradiance of the reference wave is adjusted by an attenuator 159 shown in FIG. 1, to be about a hundred times (ten times in amplitude) as intense as that of the diffraction wave at the most intense position, only a central bright spot produced by the dc term appears. A plurality of attenuators having different attenuations may be provided so that any one of them can be selectively located in the optical path to adjust attenuation. The autocorrelation of the object wave, which is supposed to appear around the central bright spot, is negligible.

In step S0420 of FIG. 4, as shown in the lower right side of FIG. 7A, a section of the object wave of N/4×N/4 elements is cut out and the size of the object to be reconstructed is restricted to D/4. The inverse Fourier transform is applied to the cut-out 2-D matrix so that the complex amplitude of the scattered wave on the pupil plane is obtained.

Figure 7B:
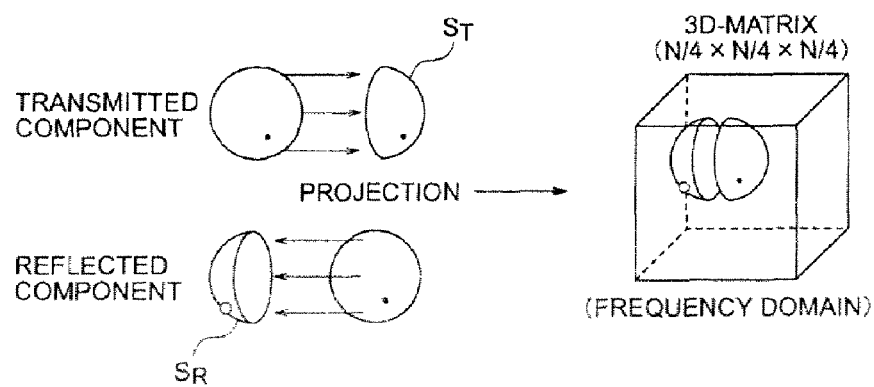
FIG. 7B illustrates a method by which a 3-D image is generated from hologram data.

In step S0430 of FIG. 4, as shown in the lower left side of FIG. 7A, a circle with diameter of N/8 is cut out. Then, as shown on the left side of FIG. 7B, each of the component of the transmitted diffracted-light and the component of the reflected diffracted-light is projected onto one of the "partial spheres" that are mapped into wave number space. It is useful to consider the detection plane of the diffracted light to correspond to wave number space, since the entrance pupils of the primary objective lenses are located at infinity and the radius of the reference sphere is also infinity (Masato Shibuya and Hiroshi Ohki; "Optics library 1 Optics of diffraction and imaging", Asakura Shoten publisher, pp. 17-24, for example). The partial spheres lie in a three-dimensional matrix of N/4× N/4×N/4 elements. As shown in FIG. 7B, the complex amplitudes in all elements other than those on the partial sphere are set to zero. In this step, the complex amplitude is projected in the z direction (the direction of the optical axis in frequency space) onto the partial sphere. If a (x, y) element of the partial sphere consists of two voxels in the z direction, the amplitude is distributed equally to the two voxels. While this step can lead to some artifacts in real space, the error is reduced by using a partial sphere convoluted with a Gaussian function containing a few elements in the z direction. After the resultant partial sphere is digitalized, the amplitude is projected onto the partial sphere with a weight of the Gaussian distribution. In this case, the peripheral intensity of the image in real space in the z direction becomes weaker.

Figure 8A:
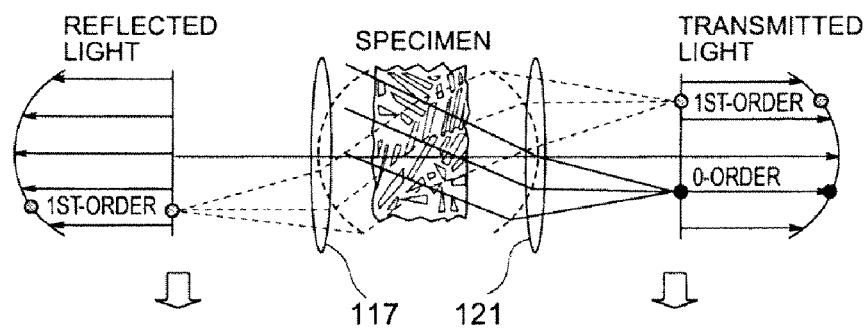
FIG. 8A illustrates a method by which a 3-D image is generated from hologram data.
Figure 8B:
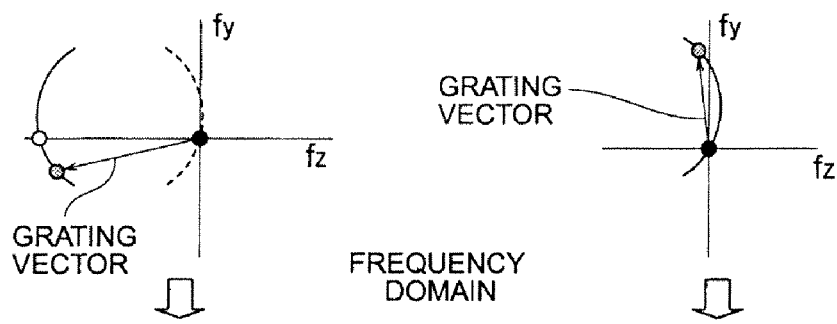
FIG. 8B illustrates a method by which a 3-D image is generated from hologram data.

As shown in FIG. 8A, the specimen is illuminated with illumination light and the 0-order light (directly transmitted light) and the transmitted diffracted-light arrive on the imaging device for transmitted diffracted-light while the reflected diffracted-light arrive on the imaging device for reflected diffracted-light. As mentioned above, an image of interference fringes generated by these diffracted lights (including 0-order light) and the reference light is obtained and complex amplitudes of diffracted lights are obtained by the processor. The complex amplitude of the transmitted diffracted-light and that of the reflected diffracted-light are respectively projected onto one of the partial spheres in the direction of the optical axis. The orientation of each partial sphere in frequency space is such that the 0-order light is placed at the frequency origin, as shown in FIG. 8B. This construction allows one to figure the physical properties of the system optical transfer function (OTF). The structure of the object is resolved into an infinite number of 3-D gratings by Fourier transform. For each grating, a vector having a direction of the normal to the grating and a magnitude corresponding to the spatial frequency of the grating is referred to as grating vector. If the system has no error in phase for the measurement of the hologram corresponding to each partial sphere, the argument of the origin in the frequency space is zero. The amplitude corresponding to the 0-order light lies on the partial sphere $S_T$ in the transmitted component. For the partial sphere $S_R$ in the reflected component, the amplitude of the 0-order light for the reflected component is located at the origin (existing on the partial sphere $S_T$ in the transmitted component), apart from the partial sphere $S_R$ in the reflected component. The partial sphere $S_R$ in the reflected component has a hole at the corresponding position where the 0-order light arrives on the two-dimensional imaging device 165. That is, the 0-order light arriving on the two-dimensional imaging device 165 for the reflected component is subtracted from the partial sphere $S_R$ in the reflected component and is used for the phase error correction of the reflected component. The partial sphere for the reflected component and the 0-order light lie on the same sphere. The two 3-D matrices for the transmitted and reflected components are combined together, which results in a matrix composed of two partial spheres facing each other. This matrix of two partial spheres, which share the same radius and center of curvature, is hereafter referred to as a twin partial sphere.

Figure 8C:
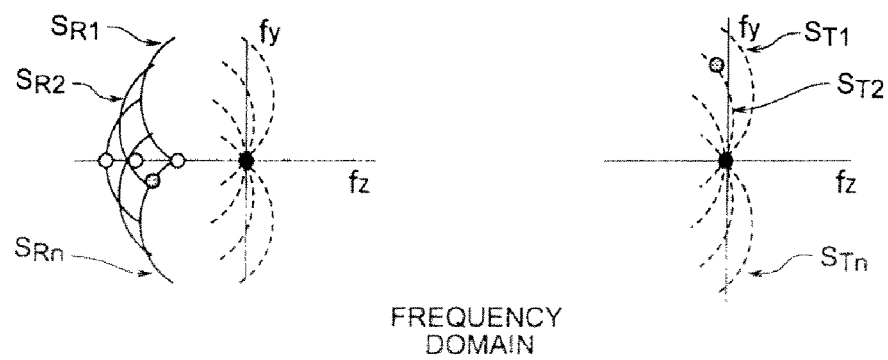
FIG. 8C illustrates a method by which a 3-D image is generated from hologram data.

In step S0440 of FIG. 4, a 3-D image of the object is obtained from the twin partial spheres. After the complex amplitudes of the twin partial spheres for all illuminating directions are calculated, each twin partial sphere is translated so that the position corresponding to the 0-order light is placed at the origin of the 3-D matrix as shown in FIG. 8C.

Changes in relative optical path length among the transmitted diffracted-light, the reflected diffracted-light and the reference light may be generated due to a temperature variation or a vibration during the measurement. A difference in phase among the measurements for each hologram could be generated. That is, the relative phase difference between the transmitted and reflected components of the twin partial sphere exists for the changes in relative optical path length among the three paths of the transmitted and reflected diffraction lights and the reference light. In order to minimize the phase error, the partial sphere for the transmitted (reflected) component is divided by the phase term of the 0-order light arriving on the two-dimensional imaging device for the transmitted (reflected) component before the two partial spheres are combined together to form the twin partial sphere. Thus, phase correction for each hologram by means of the 0-order light is achieved, and it ensures that the phase at the origin of the 3-D matrices is zero.

Further, in a looped part 110 including the specimen holder 119 and the polarization beam splitter 111, as outlined in FIG. 1, the relative optical path length between the transmitted scattered light (including the 0-order light) and the reference light may change on the order of wavelength so that a phase error caused by the change may remain. For this reason, the looped part 110 may have a solid structure.

There are two methods for obtaining a 3-D image of an object from twin partial spheres. The two methods will be described below.

FIG. 5 is a flowchart showing the first method.

In step S5010 in FIG. 5, when a 3-D image of absorptance distribution is to be obtained, the twin partial sphere is Fourier transformed and the square of the modulus is calculated for each illuminating direction. When a 3-D image of refractive index distribution is to be obtained, the twin partial sphere is Fourier transformed after the phase shift of $\pi/2$ is added only to the 0-order light, and the square of the modulus is calculated.

In step S5020 in FIG. 5, a 3-D image of distribution of the object, with the size of $D/4 \times D/4 \times D/4$ in real space is obtained by summing the squares of the moduli for all the illuminating directions. The first method corresponds to image formation with a conventional Kohler illumination system.

FIG. 6 is a flowchart showing the second method.

In step S6010 in FIG. 6, the total amplitude in the frequency domain is obtained by coherently summing the 3-D matrices of the twin partial spheres for all the illuminating directions.

In step S6020 in FIG. 6, when a 3-D image of absorptance distribution is to be obtained, a 3-D image of distribution of the object is obtained by Fourier transforming the total amplitude and taking the square of the modulus. When a 3-D image of distribution of refractive index is to be obtained, the object intensity is reconstructed by Fourier transforming the total amplitude after the phase shift of $\pi/2$ is added to the origin of the 3-D matrix, and taking the square of the modulus.

Images obtained by the first and second methods show identical optical features as long as the specimen object is a low contrast one.

For an object having refractive index distribution and absorptance distribution, 3-D microscopes according to an embodiment of the present invention separately generate a 3-D image of refractive index distribution and that of absorptance distribution.

The first and second methods will be described in further detail below.

Figure 9:
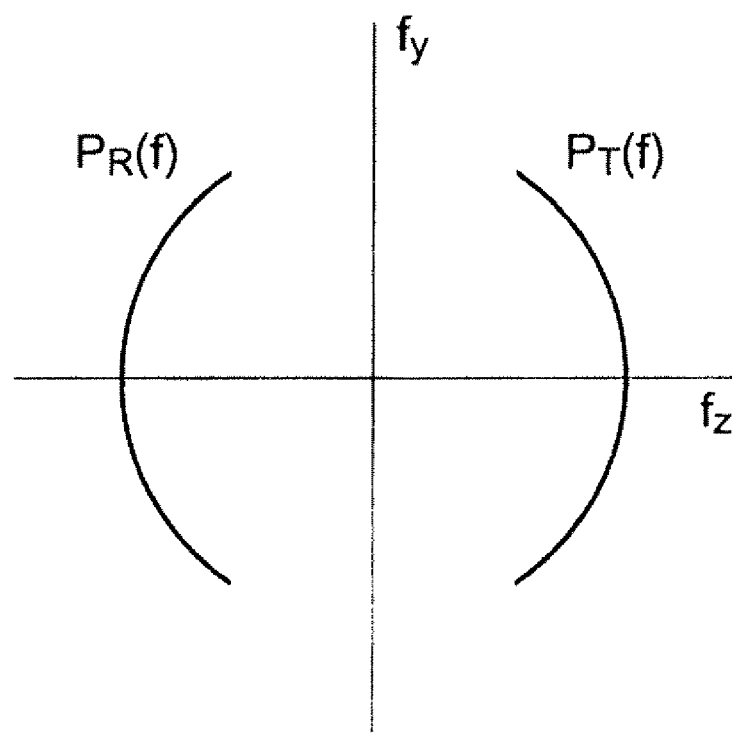
FIG. 9 shows a 3-D pupil function including two pupil functions, one on the transmission side and the other on the reflection side.

FIG. 9 shows a 3-D pupil function including two pupil functions, one on the transmission side and the other on the reflection side. The pupil function is considered to be in the frequency space.

Consider the 3-D pupil functions $P_T(f)$ for the transmission side and $P_R(f)$ for the reflection side which have the following relation.

$$P_T(f) = P^*_R(-f)$$

The asterisk stands for complex conjugate. For simplicity, it is assumed that the pupil function is unity on the partial sphere for the transmission (reflection) side and zero outside the partial sphere. That is, $$P_T(f) = \begin{cases} 1, & \text{(on shell of transmission side)} \\ 0, & \text{(others).} \end{cases}$$

$$P_R(f) = \begin{cases} 1, & \text{(on shell of reflection side)} \\ 0, & \text{(others).} \end{cases}$$

The wave number of the pump wave $2\pi f_0$ is scanned over the pupil function $P_T(f)$ and the scattered wave emerging from the object is transmitted though the both sides of the pupil $$P_T(f) = P_T(f) + P_R(f).$$

The amplitude of the 0-order light is attenuated by the attenuator (159) before arriving on the two-dimensional imaging device 165 by the factor of $0 < a < 1$. If the amplitude of the object is given by $O(x)$, the amplitude on the twin partial sphere for a certain wave number of the pump wave $2\pi f_0$ is $$F(f,f_0) = \{\int O(x)e^{-i2\pi f \cdot x}dx - a\delta(f)\}\{P_T(f+f_0) + P_R(f+f_0)\}P_T^*(f_0), \quad (4)$$

In the case of absorbing objects $O(x)$ is used without being processed, while in the case of phase objects $O(x)$ with which phase of the 0-order light is shifted by $\pi/2$. $O(x)$ can be made a real number provided that a phase of the light is selected properly.

Based on the first method, the irradiance of the image of the reconstructed object is given by $$I_1(x') = \int \left| \int F(f, f_0) e^{i2\pi f \cdot x'} df \right|^2 df_0 \quad (5)$$

$$= \int \left[ \int \{ \int O(x_1) e^{-i2\pi f_1 \cdot x_1} dx_1 - a\delta(f_1) \} \{ P_T(f_1 + f_0) + P_R(f_1 + f_0) \} P_T^*(f_0) e^{i2\pi f_2 \cdot x'} df_1 \right] \times \left[ \int \{ \int O^*(x_2) e^{i2\pi f_2 \cdot x_2} dx_2 - a\delta(f_2) \} \{ P_T^*(f_2 + f_0) + P_R^*(f_2 + f_0) \} P_T(f_0) e^{-i2\pi f_2 \cdot x'} df_2 \right] df_0$$

$$= \int \left[ \int O(x_1) P_T^*(f_0) e^{-i2\pi f_0 (x' - x_1)} \{ U_T(x' - x_1) + U_R(x' - x_1) \} dx_1 - a[P_T(f_0) + P_2(f_0)] P_T^*(f_0) \right] \times \left[ \int O^*(x_2) P_T(f_0) e^{i2\pi f_0 (x' - x_2)} \{ U_T^*(x' - x_2) + U_R^*(x' - x_2) \} dx_2 - a\{ P_T^*(f_0) + P_R^*(f_0) \} P_T(f_0) \right] df_0,$$

where $$U_T(x) = \int P_T(f) e^{i2\pi f \cdot x} df$$

$$U_R(x) = \int P_R(f) e^{i2\pi f \cdot x} df.$$

In Equation (5), square of modulus of Fourier transform of the complex amplitude is integrated with respect to illuminating direction.

The Fourier transform of the 3-D entrance pupil function $$P(f) = P_T(f) + P_R(f)$$

is equivalent to the 3-D coherent point spread function $$U(x) = U_T(x) + U_R(x),$$

which has the relations $$U_T(x) = U_R^*(x)$$

$$U_T(x) = U_T^*(-x)$$

$$U_R(x) = U_R^*(-x).$$

Since the pupil function has rotational symmetry to the optical axis, $$I_I(x') = \int\int \gamma(x_1 - x_2) O(x_1) O^*(x_2) \{ U_T(x' - x_1) + U_R(x' - x_1) \} \{ U_T^*(x' - x_2) + U_R^*(x' - x_2) \} dx_1 dx_2 - a \int O(x_1) U_R(x' - x_1) \{ U_T(x' - x_1) + U_R(x' - x_1) \} dx_1 - a \int O^*(x_2) U_T(x' - x_2) \{ U_T^*(x' - x_2) + U_R^*(x' - x_2) \} dx_2 + a^2 \int |P_T(f_0)|^4 df_0, \quad (6)$$

with $$\gamma(x_1 - x_2) = \int |P_T(f_0)|^2 e^{i2\pi f_0 (x_1 - x_2)} df_0,$$

which is referred to as the 3-D mutual intensity.

Consider a low contrast object $$O(x) = 1 + \epsilon_0 o(x)$$

where coefficient $\epsilon_0$ is a sufficiently small real number, that is $$\epsilon_0 \ll 1$$

and o(x) stands for the light scattering amplitude excluding DC component.

Inserting $$O(x) = 1 + \epsilon_0 o(x)$$

into Equation (6) yields $$I_I(x') = \int \{ 1 + \epsilon_0 o(x) + \epsilon_0^* o^*(x) \} |U_T(x' - x)|^2 dx + \quad (7)$$

$$\int \epsilon_0 o(x) U_R^2(x' - x) dx + \int \epsilon_0^* o^*(x) U_T^2(x' - x) dx -$$

$$a \int \{ 1 + \epsilon_0 o(x) \} \{ |U_T(x' - x)|^2 + U_R^2(x' - x) \} dx -$$

$$a \int \{ 1 + \epsilon_0^* o^*(x) \} \{ |U_T(x' - x)|^2 + U_T^2(x' - x) \} dx +$$

$$a^2 \int |U_T(x' - x)|^2 dx,$$

where Parseval's theorem $$\int |P_T(f_0)|^2 df_0 = \int |U_T(x' - x)|^2 dx$$

and $$|P_T(f_0)|^4 = |P_T(f_0)|^2$$

are used in the last term and the second order terms of $\epsilon_0$ are ignored. A further simple calculation leads to $$I_I(x') = (1-a)\left[ (1-a) \int |U_T(x' - x)|^2 dx + \right. \quad (8)$$

$$\int \epsilon_0 o(x) \{ |U_T(x' - x)|^2 + U_R^2(x' - x) \} dx +$$

$$\left. \int \epsilon_0^* o^*(x) \{ |U_T(x' - x)|^2 + U_T^2(x' - x) \} dx \right]$$

$$= (1-a) \int |U_T(x)|^2 dx [(1-a) +$$

$$\epsilon_0 \int \tilde{o}(f) OTF(f) e^{i2\pi f \cdot x} df +$$

$$\epsilon_0^* \int \tilde{o}^*(f) OTF^*(f) e^{-i2\pi f \cdot x} df],$$

where $$\int U_R^2(x' - x) dx - \int U_T^2(x' - x) dx = 0$$

and $\tilde{o}(f)$ is the Fourier transformer of o(x). The 3-D optical transfer function is defined as $$OTF(f) = \frac{\int \{ |U_T(x)|^2 + U_R^2(x) \} e^{-i2\pi f \cdot x} dx}{\int |U_T(x)|^2 dx},$$

which is equivalent to the correlation function between the entrance pupil $$P(f) = P_T(f) + P_R(f)$$

and the pupil on transmission side $P_T(f)$ for lights from the light source, that is $$OTF(f) = \frac{\int P(f')P_T^*(f'-f)df'}{\int |P_T(f')|^2 df'}.$$

Figure 10:
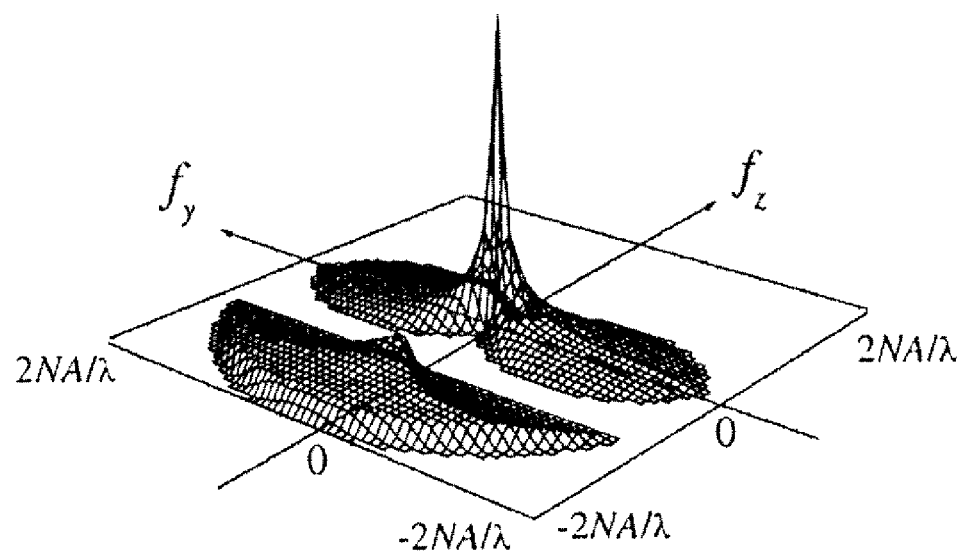
FIG. 10 shows the OTF in the case for NA=1.2 with the primary objective lens in water.

FIG. 10 shows the OTF in the case for NA=1.2 with the primary objective lens in water. The OTF has rotational symmetry in the $f_Z$ direction, which is the spatial frequency in the direction of the optical axis. A cross section involving the $f_Z$ axis is described in FIG. 10. Note that spatial frequencies along the optical axis cannot be resolved for both the transmitted and reflected components, since the scattered wave propagated in the vicinity of the 0-order light is intercepted by the micromirror 137, which is similar to the conventional phase contrast microscopy. The depth resolution is gained from the reflected component, and a part of the OTF corresponding to the reflected component lies in the region known as the missing cone. Although the gap between the two portions of the OTF corresponding to the transmitted and reflected components exists and the spatial frequency in the gap cannot be resolved, it can be reduced by using higher NA objective lenses.

If the amplitude of the object is a real-valued function $$O(x)=O^*(x),$$

which holds for a 3-D phase object with a low contrast refractive index distribution, Equation (8) is represented as $$I_l(x') = (1-a)^2 \int |U_T(x'-x)|^2 dx + (1-a) \int \varepsilon_0 o(x)\{2|U_T(x'-x)|^2 + U_R^2(x'-x) + U_T^2(x'-x)\}dx \quad (9)$$

$$= (1-a)\left[\int \{(1-a) + 2\varepsilon_0 o(x)\} PSF(x'-x)/2dx\right],$$

where $$PSF(x'-x) = 2|U_T(x'-x)|^2 + U_R^2(x'-x) + U_T^2(x'-x)$$
$$= |U(x'-x)|^2$$

is the 3-D point spread function. Intensity of the low contrast object $$|O(x)|^2 = 1 + 2\varepsilon_0 o(x)$$

is converted into $$|O_a(x)|^2 = (1-\alpha) + 2\varepsilon_0 o(x)$$

which means that the initial contrast of the object $2\varepsilon_0$ is enhanced to $2\varepsilon_0/(1-\alpha)$ by attenuation of the 0-order light. Finally, a simple equation for object reconstruction is obtained, $$I_l(x') = (1-\alpha)\{\int |O_a(x)|^2 PSF(x'-x)/2dx\} \quad (10)$$

The irradiance of the image reconstructed through this algorithm is represented by the convolution of the object intensity, which has the enhanced contrast, with the 3-D point spread function.

In the second method, the irradiance of the image is given by $$I_n(x') = \left|\int\left\{\int F(f, f_0)df_0\right\}e^{i2\pi f \cdot x'}df\right|^2 \quad (11)$$

$$= \left|\int\left[\int\left\{\int O(x)e^{-i2\pi f \cdot x}dx - a\delta(f)\right\}\{P_T(f+f_0) + P_R(f+f_0)\}P_T^*(f_0)df_0\right]e^{i2\pi f \cdot x'}df\right|^2$$

$$= \left|\int O(x)U_R(x'-x)\{U_T(x'-x) + U_R(x'-x)\}dx - a\int |P_T(f_0)|^2 df_0\right|^2$$

$$= \left|\int O(x)\{|U_T(x'-x)|^2 + U_R^2(x'-x)\}dx - a\int |U_T(x'-x)|^2 dx\right|^2,$$

where Parseval's theorem is used. In Equation (11), complex amplitude is integrated with respect to illuminating direction and then the integrated value is Fourier transformed and a square of modulus of the Fourier transformed value. If the sample is a low contrast object, substituting $$O(x) = 1 + \varepsilon_0 o(x)$$

into Equation (11) yields $$I_u(x') = \left|\int\{1 + \varepsilon_0 o(x)\}\{|U_T(x'-x)|^2 + U_R^2(x'-x)\}dx - a\int |U_T(x'-x)|^2 dx\right|^2 \quad (12)$$

$$= A(1-a)\left[(1-a)\int |U_T(x'-x)|^2 dx + \int \varepsilon_0 o(x)\{|U_T(x'-x)|^2 + U_R^2(x'-x)\}dx + \int \varepsilon_0^* o^*(x)\{|U_T(x'-x)|^2 + U_T^2(x'-x)\}dx\right]$$

$$= AI_l(x')$$

where $$A = \int |U_T(x'-x)|^2 dx$$

and the second order terms of $\varepsilon_0$ are ignored. The image irradiance of the reconstructed object through the second method is proportional to that of the first algorithm, as long as the sample is a low contrast object. The second method can reduce the computing time, because it requires only one 3-D Fourier transform in the final stage.

The image can be deconvoluted with the OTF in the same way as a conventional optical system. In the first method, each shifted partial sphere is divided by the OTF before it is Fourier transformed. In the second method, the deconvolution is achieved by dividing the total amplitude in the frequency domain by the OTF before taking the square of the modulus. Both methods are phase error free in the transmitted component, so low-frequency objects can be resolved with almost no error in reconstruction.

Features of the embodiments of the present invention will be described below.

The feature of an embodiment of the present invention is that a three-dimensional image of absorptance distribution of the object and a three-dimensional image of refractive index distribution of the object are generated from the interference images for respective illuminating directions.

According to the embodiment, for an object having absorptance distribution and refractive index distribution, a three-dimensional image of absorptance distribution and a three-dimensional image of refractive index distribution can be separately obtained.

The feature of another embodiment of the present invention is that transmitted diffracted-lights and reflected diffracted-lights are used as the diffracted lights.

According to the embodiment, higher resolution in the depth direction can be obtained by the use of transmitted diffracted-lights and reflected diffracted-lights as the diffracted lights.

The feature of another embodiment of the present invention is that 0-order lights that have transmitted thorough the object are used as the reference lights.

According to the embodiment, a simple-structured optical system can be made by the use of the 0-order lights as the reference lights.

The feature of another embodiment of the present invention is that the 0-order lights used as the reference lights are attenuated on the path.

According to the embodiment, saturation of the imaging section with the 0-order lights intensity of which is larger than that of the diffracted lights, is prevented by attenuating the 0-order lights used as the reference lights, on the path.

The feature of another embodiment of the present invention is that a portion of the 0-order lights is separated from the 0-order lights to be used as the reference lights and is made to travel along the same path as that of the diffracted lights and phase errors between the diffracted lights and the reference lights are corrected using phases of the 0-order lights having traveled along the same path as that of the diffracted lights when generating the three-dimensional image from the interference images.

According to the embodiment, phase errors between different interferences can be minimized.

The feature of another embodiment of the present invention is that a mirror for reflecting the lights is provided, illuminating directions of the lights are changed by tilting the mirror and the mirror is located at a conjugate position of the object so that the 0-order lights reflected on the mirror converge to the center of a Fourier plane of the object, independently of illuminating directions.

According to the embodiment, the 0-order lights reflected on the mirror converge to the center of a Fourier plane of the object, independently of illuminating directions and therefore are conveniently used as the reference lights.

The feature of another embodiment of the present invention is that a micromirror is located at the center of the Fourier plane of the object so that the micromirror reflects the 0-order lights used as the reference lights to separate a path of the 0-order lights used as the reference lights from a path of the diffracted lights.

According to the embodiment, a path of the 0-order lights used as the reference lights can be separated from a path of the diffracted lights by a simple structure.

The invention claimed is:

1. A three-dimensional microscope comprising;
a first optical system for illuminating an object with lights in a plurality of illuminating directions, one direction after another;
an imaging section;
a second optical system for guiding diffracted lights generated by said object and reference lights to said imaging section that obtains interference images of said diffracted lights and said reference lights; and
a processor for generating a three-dimensional image using said interference images for respective illuminating directions, obtained by said imaging section, wherein
said processor obtains complex amplitudes of said diffracted lights from said interference images for respective illuminating directions and generates the three-dimensional image of the object from said complex amplitudes.

2. A three-dimensional microscope according to claim 1 wherein said processor is arranged to generate a three-dimensional image of absorptance distribution of said object and a three-dimensional image of refractive index distribution of said object from said interference images for respective illuminating directions.

3. A three-dimensional microscope according to claim 1, arranged to use transmitted diffracted-lights and reflected diffracted-lights as said diffracted lights.

4. A three-dimensional microscope according to claim 1, arranged to use 0-order lights that have transmitted thorough said object as said reference lights.

5. A three-dimensional microscope according to claim 4, wherein an attenuator is provided in said second optical system so that said imaging section may not be saturated with the 0-order lights used as said reference lights.

6. A three-dimensional microscope according to claim 4, wherein said second optical system is arranged in such a way that a portion of the 0-order lights is separated from the 0-order lights to be used as said reference lights, travels along the same path as that of said diffracted lights and arrives on said imaging section and said processor is arranged to correct phase errors between said diffracted lights and said reference lights using phases of the 0-order lights having traveled along the same path as that of said diffracted lights and arrived on said imaging section.

7. A three-dimensional microscope according to claim 4, wherein said second optical system is provide with a mirror for reflecting said lights and arranged to change illuminating directions of said lights by tilting said mirror and said mirror is located at a conjugate position of said object so that the 0-order lights reflected on said mirror converge to the center of a Fourier plane of said object, independently of illuminating directions.

8. A three-dimensional microscope according to claim 7, wherein a micromirror is located at the center of the Fourier plane of said object so that said micromirror reflects the 0-order lights used as said reference lights to separate the path of the 0-order lights used as said reference lights from the path of said diffracted lights.

9. A method for generating a three-dimensional image of an object using digital holography, the method comprising:
illuminating said object in a plurality of illuminating directions, one direction after another;
obtaining interference images of diffracted lights generated by said object and reference lights, for respective illuminating directions;
obtaining complex amplitudes of said diffracted lights from said interference images obtained for respective illuminating directions; and
generating the three-dimensional image of said object from said complex amplitudes.

10. A method for generating a three-dimensional image according to claim 9 wherein a three-dimensional image of absorptance distribution of said object and a three-dimensional image of refractive index distribution of said object are generated from said interference images for respective illuminating directions.

11. A method for generating a three-dimensional image according to claim 9 wherein transmitted diffracted-lights and reflected diffracted-lights are used as said diffracted lights.

12. A method for generating a three-dimensional image according to claim 9 wherein 0-order lights are used as said reference lights.

13. A method for generating a three-dimensional image according to claim 12 wherein the 0-order lights used as said reference lights are attenuated on the path.

14. A method for generating a three-dimensional image according to claim 12 wherein a portion of the 0-order lights is separated from the 0-order lights to be used as said reference lights and is made to travel along the same path as that of said diffracted lights and phase errors between said diffracted lights and said reference lights are corrected using phases of the 0-order lights having traveled along the same path as that of said diffracted lights when generating the three-dimensional image from said interference images.

15. A method for generating a three-dimensional image according to claim 12 wherein a mirror for reflecting said lights is provided, illuminating directions of said lights are changed by tilting said mirror and said mirror is located at a conjugate position of said object so that the 0-order lights reflected on said mirror converge to the center of a Fourier plane of said object, independently of illuminating directions.

16. A method for generating a three-dimensional image according to claim 15 wherein a micromirror is located at the center of the Fourier plane of said object so that said micromirror reflects the 0-order lights used as said reference lights to separate a path of the 0-order lights used as said reference lights from a path of said diffracted lights.

\* \* \* \* \*